US00PP32499P3

(12) United States Plant Patent
Jacobs, III et al.

(10) Patent No.: US PP32,499 P3
(45) Date of Patent: Nov. 24, 2020

(54) STRAWBERRY PLANT NAMED 'DRISSTRAWSEVENTY'

(50) Latin Name: *Fragaria x ananassa*
Varietal Denomination: DrisStrawSeventy

(71) Applicant: Driscoll's, Inc., Watsonville, CA (US)

(72) Inventors: Raymond L. Jacobs, III, Watsonville, CA (US); Esther Kibbe, Alden, CA (US); Philip J. Stewart, Watsonville, CA (US); Mary M. Calkins, Plant City, FL (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 16/501,501

(22) Filed: Apr. 18, 2019

(65) Prior Publication Data

US 2020/0337195 P1 Oct. 22, 2020

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409
See application file for complete search history.

(56) References Cited

U.S. PATENT DOCUMENTS

PP1,745 P 8/1958 Lang
PP3,981 P 11/1976 Bringhurst et al.
PP4,487 P 11/1979 Bringhurst et al.
PP4,538 P 5/1980 Bringhurst et al.
PP5,262 P 7/1984 Voth et al.
PP5,265 P 7/1984 Voth et al.
PP5,266 P 7/1984 Bringhurst et al.
PP5,300 P 10/1984 Johnson Jr.
PP5,480 P 5/1985 Nakagawa
PP5,840 P 12/1986 Johnson, Jr. et al.
PP6,191 P 5/1988 Johnson, Jr. et al.
PP6,231 P 7/1988 Johnson, Jr. et al.
PP6,578 P 1/1989 Voth et al.
PP6,579 P 1/1989 Bringhurst et al.
PP7,024 P 9/1989 Johnson, Jr. et al.
PP7,172 P 2/1990 Voth et al.
PP7,522 P 5/1991 Johnson, Jr. et al.
PP7,614 P 8/1991 Bringhurst et al.
PP7,615 P 8/1991 Bringhurst et al.
PP8,086 P 1/1993 Nelson et al.
PP8,205 P 4/1993 Nelson et al.
PP8,649 P 3/1994 Sjulin et al.
PP8,661 P 3/1994 Bringhurst et al.
PP8,708 P 5/1994 Voth et al.
PP8,745 P 5/1994 Sjulin et al.
PP9,130 P 5/1995 Sjulin et al.
PP9,909 P 6/1997 Ackerman et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,889 P2 8/2002 Lamb et al.
PP12,899 P2 9/2002 Mowrey et al.
PP13,386 P2 12/2002 Mowrey et al.
PP13,469 P3 1/2003 Larson et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP16,558 P3 5/2006 López
PP18,000 P2 9/2007 Meulenbroek
PP18,040 P3 9/2007 Mowrey et al.
PP18,041 P3 9/2007 Gilford
PP18,458 P2 1/2008 Ferguson et al.
PP18,575 P3 3/2008 Amorao et al.
(Continued)

OTHER PUBLICATIONS

"An Early Season with Many highs", Berry Gardens, Available Online at <https://www.berrygardens.co.uk/an-early-season-with-many-highs/>, Aug. 21, 2017, pp. 1-6.

(Continued)

*Primary Examiner* — Anne Marie Grunberg

(74) *Attorney, Agent, or Firm* — Morrison & Foerster LLP

(57) ABSTRACT

A new and distinct variety of strawberry plant named 'DrisStrawSeventy', selected for its fruit size, consistency of size and shape of fruit, fruit glossiness and appearance, fruit eating quality, flavor, and texture, partially remontant type of bearing with yield from both early and late fruiting, plant architecture, plant vigor, and long fruit trusses, is disclosed.

7 Drawing Sheets

(56) References Cited

U.S. PATENT DOCUMENTS

| | | | |
|---|---|---|---|
| PP18,878 | P2 | 6/2008 | Mowrey et al. |
| PP19,240 | P2 | 9/2008 | Gilford et al. |
| PP19,673 | P3 | 2/2009 | Ferguson et al. |
| PP19,767 | P2 | 2/2009 | Shaw et al. |
| PP20,248 | P3 | 9/2009 | Rogers et al. |
| PP20,363 | P2 | 9/2009 | Chandler |
| PP20,701 | P2 | 2/2010 | Gilford et al. |
| PP20,731 | P2 | 2/2010 | Mowrey et al. |
| PP20,733 | P2 | 2/2010 | Mowrey et al. |
| PP20,735 | P2 | 2/2010 | Ferguson |
| PP20,775 | P2 | 2/2010 | Mowrey et al. |
| PP20,922 | P2 | 4/2010 | Gilford et al. |
| PP21,538 | P2 | 11/2010 | Gilford et al. |
| PP21,559 | P2 | 12/2010 | Ferguson et al. |
| PP21,762 | P2 | 3/2011 | Stewart et al. |
| PP22,040 | P3 | 7/2011 | Stewart et al. |
| PP22,218 | P2 | 11/2011 | Ferguson |
| PP22,247 | P2 | 11/2011 | Ferguson |
| PP23,107 | P2 | 10/2012 | Ferguson et al. |
| PP23,148 | P2 | 10/2012 | Gilford et al. |
| PP23,377 | P2 | 2/2013 | Ferguson et al. |
| PP23,378 | P2 | 2/2013 | Pullen et al. |
| PP23,382 | P2 | 2/2013 | Ferguson et al. |
| PP23,383 | P2 | 2/2013 | Ferguson et al. |
| PP23,400 | P2 | 2/2013 | Ferguson et al. |
| PP23,401 | P2 | 2/2013 | Pullen et al. |
| PP23,459 | P2 | 3/2013 | Stewart et al. |
| PP23,506 | P3 | 4/2013 | Ferguson et al. |
| PP23,517 | P3 | 4/2013 | Ferguson et al. |
| PP24,096 | P3 | 12/2013 | Fear et al. |
| PP24,317 | P3 | 3/2014 | Ferguson et al. |
| PP24,333 | P3 | 3/2014 | Vitten et al. |
| PP24,395 | P3 | 4/2014 | Vitten et al. |
| PP24,533 | P3 | 6/2014 | Ferguson et al. |
| PP24,745 | P2 | 8/2014 | Vitten et al. |
| PP25,408 | P3 | 4/2015 | Vitten et al. |
| PP25,437 | P3 | 4/2015 | Vitten et al. |
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| 2003/0079263 | P1 | 4/2003 | Gilford et al. |
| 2013/0276182 | P1 | 10/2013 | Fear et al. |

OTHER PUBLICATIONS

Fear et al., Unpublished U.S. Appl. No. 15/998,014, filed Jun. 11, 2018, titled "Strawberry Plant Variety Named 'DrisStrawFiftyEight'".

Ferguson et al., Unpublished U.S. Appl. No. 15/998,317, filed Aug. 3, 2018, titled "Strawberry Plant Variety Named 'DrisStrawSixty'".

Ferguson et al., Unpublished U.S. Appl. No. 16/501,428, filed Apr. 12, 2019, titled "Strawberry Plant Variety Named 'DrisStrawSeventyFive'".

Katie, "My Green Pod", Available online at <https://www.mygreenpod.com/articles/its-strawberry-time/>, May 30, 2017, pp. 1-3.

Mendoza et al., Unpublished U.S. Appl. No. 16/350,139, filed Oct. 2, 2018, titled "Strawberry Plant Variety Named 'DrisStrawSixtySeven'".

Mendoza et al., Unpublished U.S. Appl. No. 15/998,020, filed Jun. 12, 2018, titled "Strawberry Plant Variety Named 'DrisStrawSixtyOne'".

Mendoza et al., Unpublished U.S. Appl. No. 15/998,169, filed Jul. 12, 2018, titled "Strawberry Plant Variety Named 'DrisStrawSixtyThree'".

Mendoza et al., Unpublished U.S. Appl. No. 15/998,170, filed Jul. 12, 2018, titled "Strawberry Plant Variety Named 'DrisStrawSixtyTwo'".

Pakozdi et al., Unpublished U.S. Appl. No. 16/501,198, filed Mar. 5, 2019, titled "Strawberry Plant Variety Named 'DrisStrawSeventyThree'".

Pakozdi et al., Unpublished U.S. Appl. No. 15/998,015, filed Jun. 11, 2018, titled "Strawberry Plant Variety Named 'DrisStrawFiftyNine'".

Pakozdi et al., Unpublished U.S. Appl. No. 15/998,028, filed Jun. 14, 2018, titled "Strawberry Plant Variety Named 'DrisStrawSixtyFive'".

Pakozdi et al., Unpublished U.S. Appl. No. 16/501,182, filed Mar. 5, 2019, titled "Strawberry Plant Variety Named 'DrisStrawSeventyFour'".

Pakozdi et al., Unpublished U.S. Appl. No. 16/501,200, filed Mar. 5, 2019, titled "Strawberry Plant Variety Named 'DrisStrawSeventyTwo'".

Stewart et al., Unpublished U.S. Appl. No. 16/350,432, filed Nov. 14, 2018, titled "Strawberry Plant Variety Named 'DrisStrawSixtySix'".

Stewart et al., Unpublished U.S. Appl. No. 15/998,031, filed Jun. 14, 2018, titled "Strawberry Plant Variety Named 'DrisStrawSixtyFour'".

Stewart et al., Unpublished U.S. Appl. No. 16/501,449, filed Apr. 17, 2019, titled "Strawberry Plant Variety Named 'DrisStrawSeventyOne'".

STRAWBERRY PLANT NAMED 'DRISSTRAWSEVENTY'

Latin name:

Botanical classification: *Fragaria* x *ananassa*.

Varietal denomination: The varietal denomination of the claimed variety of strawberry plant is 'DrisStrawSeventy'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawSeventy'.

Strawberry plant variety 'DrisStrawSeventy' originated from a cross between the proprietary female parent '139T272' (unpatented) and the male parent 'DrisStrawTwentyFour' (U.S. Plant Pat. No. 23,378). Progeny plants from this cross, including 'DrisStrawSeventy', were asexually propagated via stolons in McArthur, Shasta County, Calif. in September of 2012. Strawberry plant variety 'DrisStrawSeventy' was later specifically identified and selected in Hillsborough County, Fla. in January of 2013.

'DrisStrawSeventy' was subsequently asexually propagated via stolons, and underwent further testing at a farm in Hillsborough County, Fla. for six years (2013 to 2018). The present variety has been found to be stable and reproduce true to type through successive asexual propagations via stolons.

'DrisStrawSeventy' exhibits the following distinguishing characteristics when grown under normal horticultural practices in Hillsborough County, Fla.:

1. Semi-upright plant growth habit;
2. Inflorescence above foliage; and
3. Calyx attachment level with fruit.

'DrisStrawSeventy' was selected for its fruit size, consistency of size and shape of fruit, fruit glossiness and appearance, fruit eating quality, flavor, and texture, partially remontant type of bearing with yield from both early and late fruiting, plant architecture, plant vigor, and long fruit trusses.

DESCRIPTION OF THE DRAWINGS

This new strawberry plant is illustrated by the accompanying photographs which show fruit of the plant, flowers, leaves, and plants in the field. The colors shown are as true as can be reasonably obtained by conventional photographic procedures. The photographs are of plants that are four months from time of transplant at nursery.

DETAILED BOTANICAL DESCRIPTION OF THE PLANT

Figure 1:
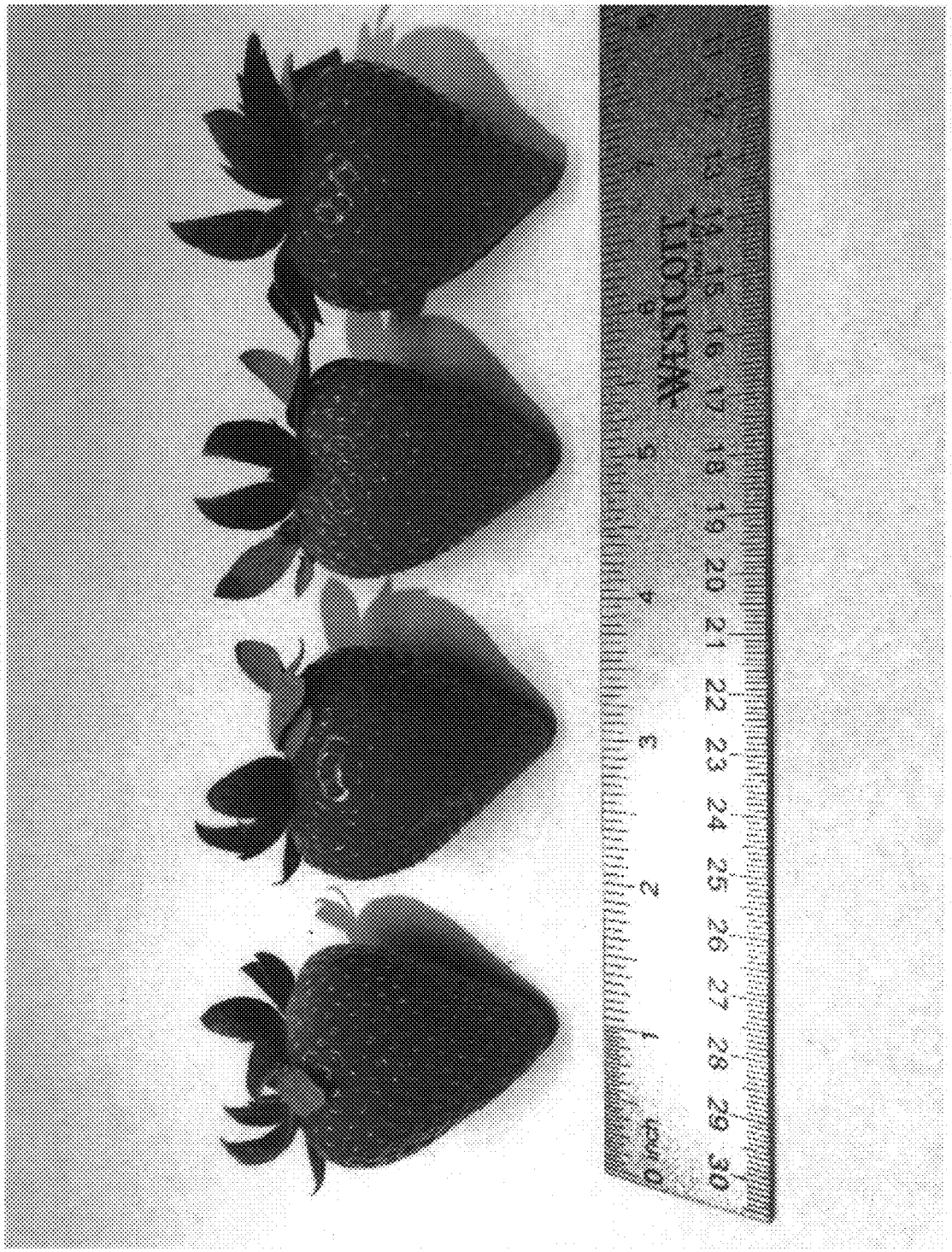
FIG. 1 illustrates whole fruit of variety 'DrisStrawSeventy'.
Figure 2:
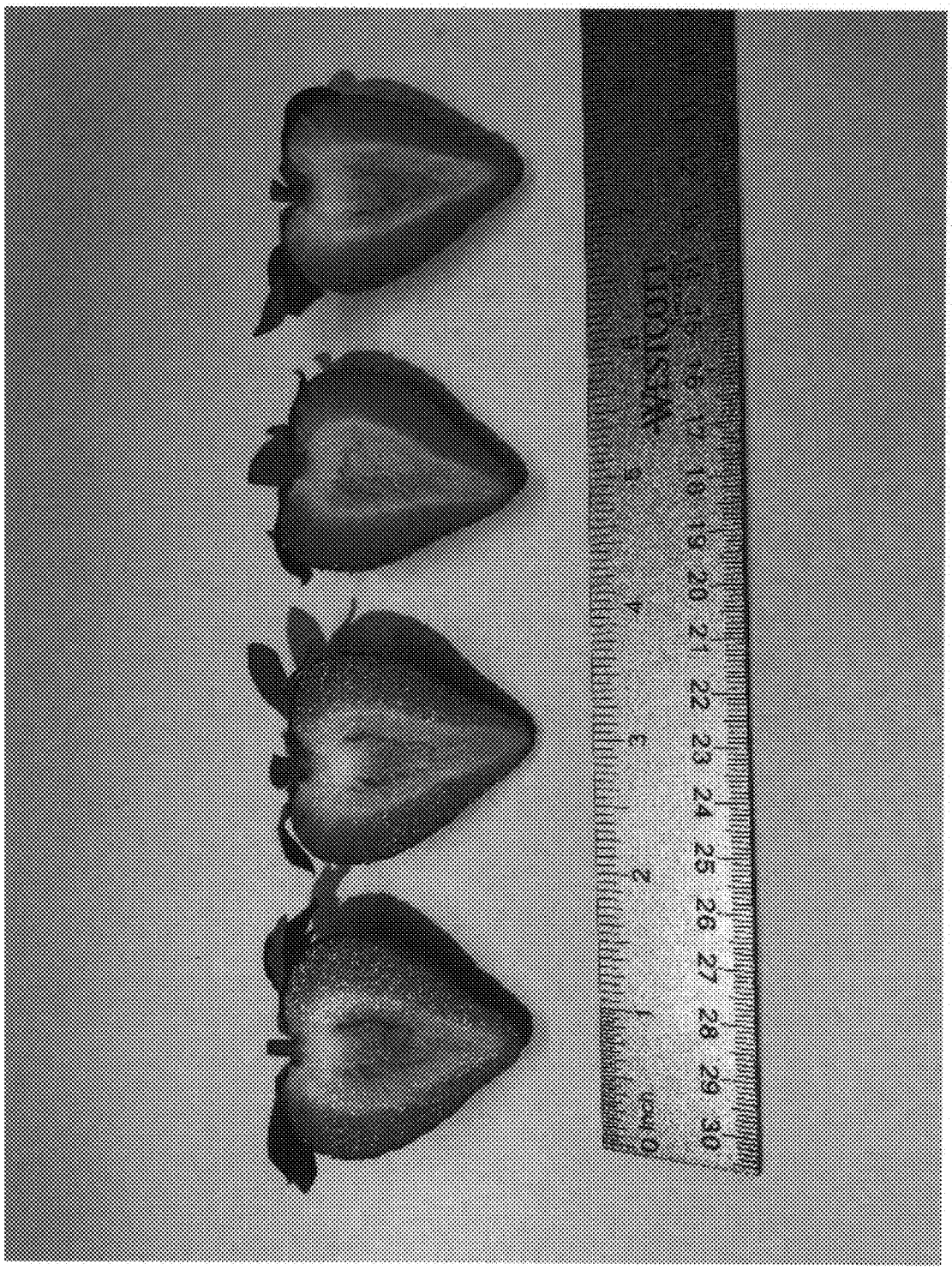
FIG. 2 illustrates longitudinal sections of fruit of variety 'DrisStrawSeventy'.
Figure 3:
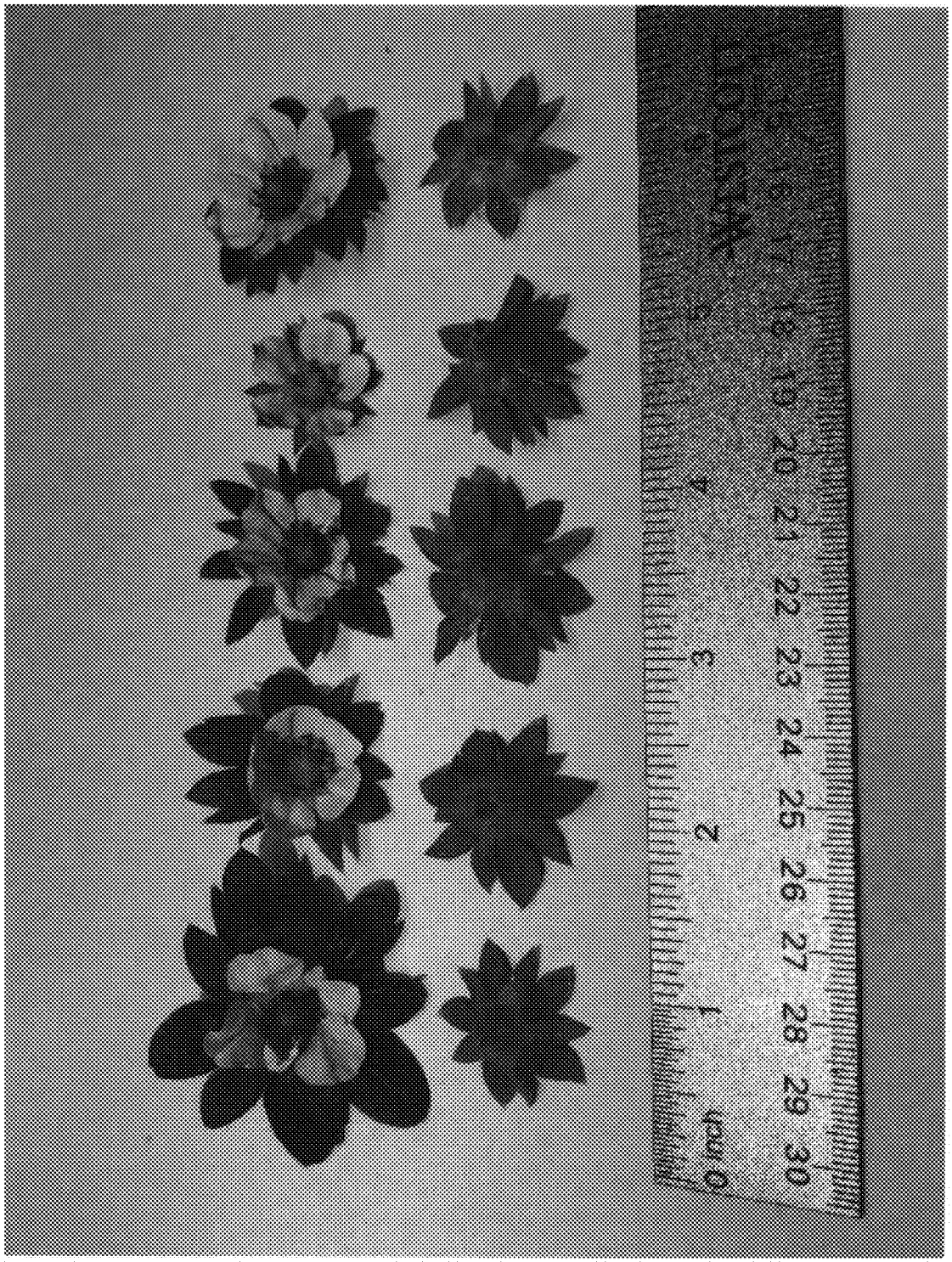
FIG. 3 shows the upper and lower surfaces of flowers of variety 'DrisStrawSeventy'.
Figure 4:
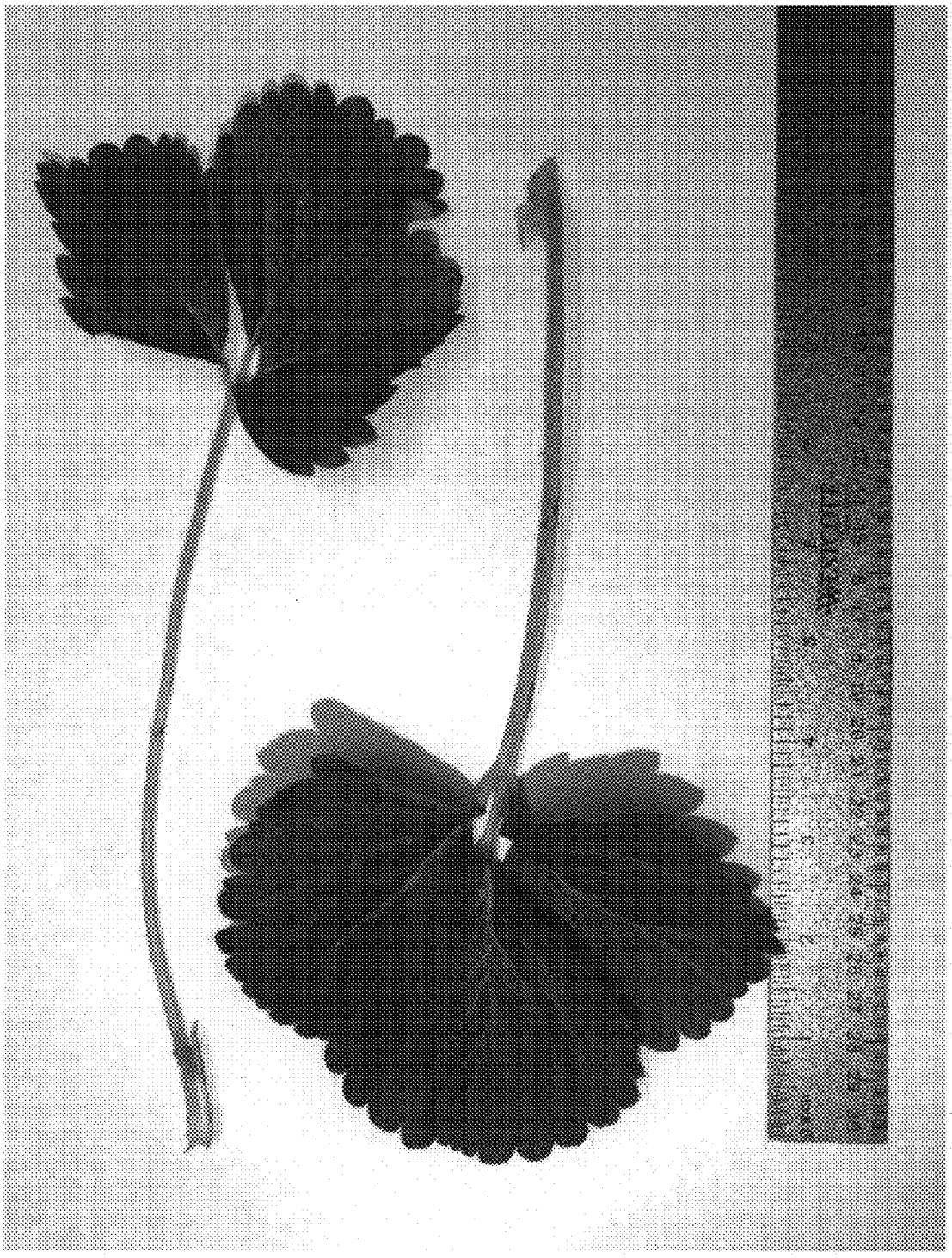
FIG. 4 shows the upper surface of leaves of variety 'DrisStrawSeventy'.
Figure 5:
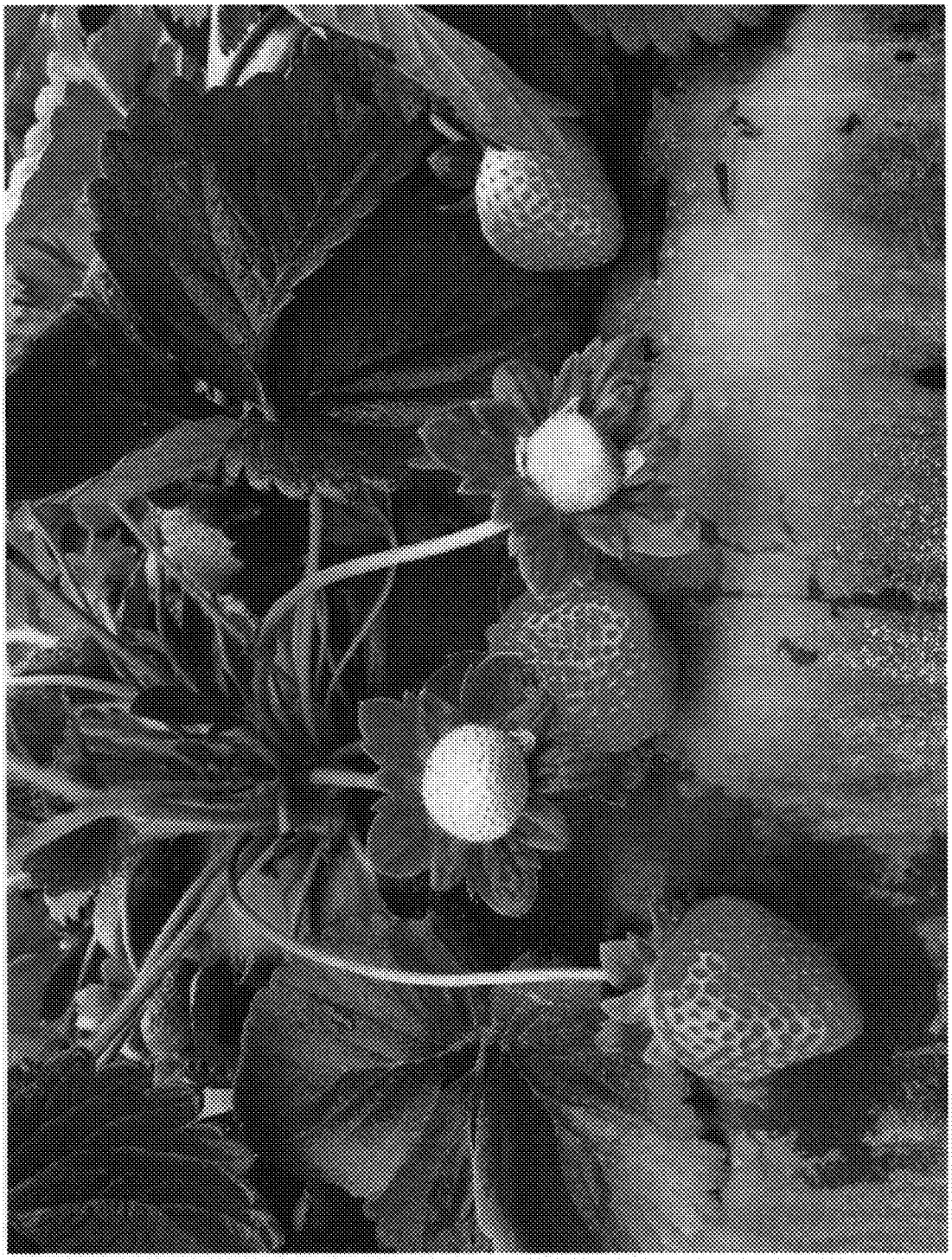
FIG. 5 illustrates fruit of variety 'DrisStrawSeventy' at different maturation stages.
Figure 6:
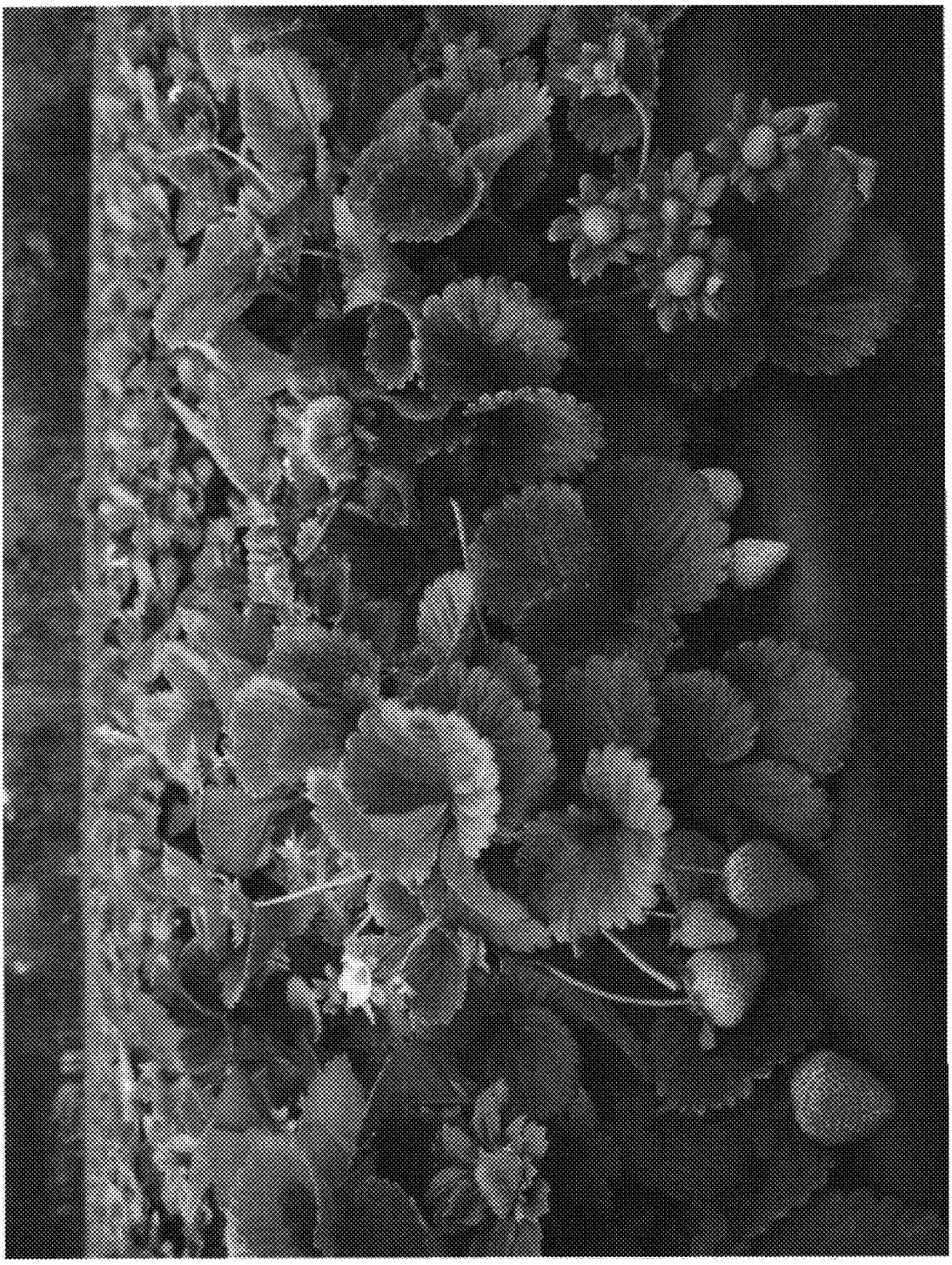
FIG. 6 illustrates plants of variety 'DrisStrawSeventy'.
Figure 7:
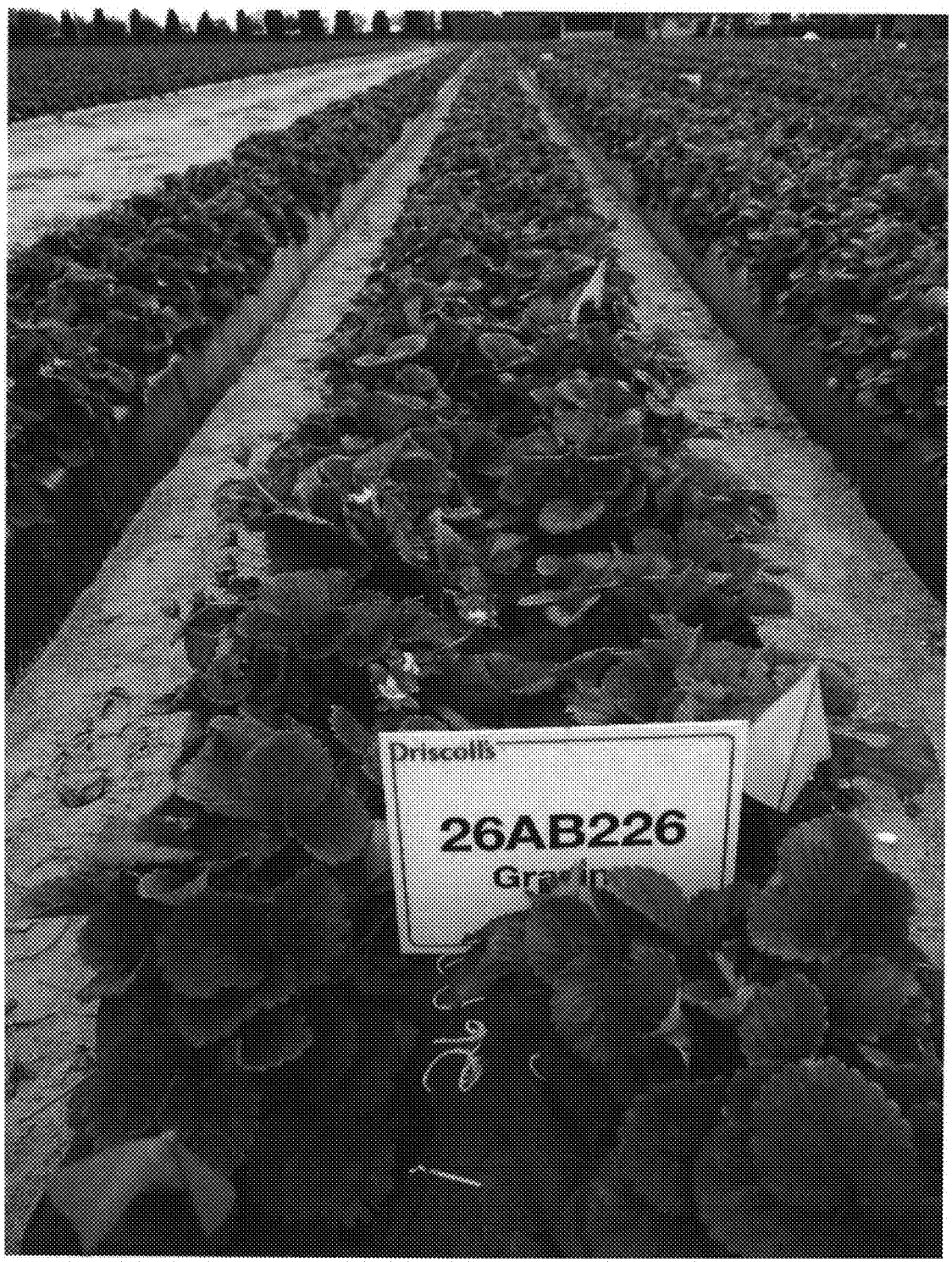
FIG. 7 illustrates a field of variety 'DrisStrawSeventy'.

The following detailed descriptions set forth the distinctive characteristics of 'DrisStrawSeventy'. The data which define these characteristics is based on observations taken in Hillsborough County, Fla. from 2013 to 2018. This description is in accordance with UPOV terminology. Color designations, color descriptions, and other phenotypical descriptions may deviate from the stated values and descriptions depending upon variation in environmental, seasonal, climatic, and cultural conditions. 'DrisStrawSeventy' has not been observed under all possible environmental conditions. The botanical description of 'DrisStrawSeventy' was taken from plants that were four month from time of transplant at nursery. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawSeventy'.

Parentage:

*Female parent.*—The proprietary variety '139T272' (unpatented).

*Male parent.*—The variety 'DrisStrawTwentyFour' (U.S. Plant Pat. No. 23,378).

Plant:

*Height.*—22.4 cm.

*Diameter.*—33.2 cm.

*Number of crowns per plant.*—2.4.

*Growth habit.*—Semi-upright.

*Density of foliage.*—Medium.

*Vigor.*—Medium.

Stolon:

*Average number of daughter plants per square foot.*—10.

*Diameter at bract.*—3.41 mm.

*Density of pubescence.*—Sparse.

*Stolon color.*—RHS 144B (Strong yellow-green).

*Anthocyanin coloration.*—Strong.

*Anthocyanin color.*—RHS 50B (Deep pink).

Leaf:

*Number of leaflets.*—Three only.

*Color of upper surface.*—RHS 137A (Moderate olive green).

*Color of lower surface.*—RHS 139C (Moderate yellowish green).

*Blistering.*—Medium.

*Glossiness.*—Medium.

*Variegation.*—Absent.

*Terminal leaflets.*—Length: 8.3 cm. Width: 7.9 cm. Length/width ratio: 1.0. Number of teeth/terminal leaflet: 19.6. Leaflet shape: Orbicular. Leaflet apex: Rounded. Shape of base: Obtuse. Margin: Crenate. Shape in cross section: Straight.

*Petiole.*—Color of petiole: RHS 150C (Brilliant yellowish green). Length: 15.3 cm. Diameter: 2.9 mm. Attitude of hairs: Horizontal. Bract frequency (number present on each petiole): 1.1.

*Petiolule.*—Color of petiolule: RHS 150C (Brilliant yellowish green). Length: 12.0 mm. Diameter: 1.6 mm.

*Stipule.*—Length: 2.8 cm. Width: 8.2 mm. Stipule color: RHS 63A (Strong purplish red). Anthocyanin coloration: Medium. Anthocyanin color: RHS 47A (Moderate red).

Inflorescence:

*Position in relation to foliage.*—Above.

*Pedicel.*—Pedicel length: 21.25 cm. Pedicel diameter: 2.11 mm. Color of pedicel: RHS 150C (Brilliant yellowish green). Attitude of hairs: Upwards.

*Flower.*—Flower depth: 11.0 mm. Flower diameter (petal tip to petal tip on non-flattened flower): 25.79 mm. Arrangement of petals: Overlapping. Stamen: Present. Stamen length: 1.97 mm. Stamen width: 0.5 mm. Stamen shape: Dorsifixed. Stamen color: RHS 1C (Light greenish yellow). Number of stamens per flower: 27.6. Anther color: RHS 13A (Vivid yellow). Typical and observed number of flowers per plant: 3.30.

*Petal.*—Petal shape: Orbicular. Petal apex: Rounded. Petal margin: Smooth. Petal base: Concave to convex. Length: 9.90 mm. Width: 10.37 mm. Length/width ratio: 1.0. Typical and observed petal number: 5.7. Color of upper side: RHS 155C (Greenish white). Color of lower side: RHS 155C (Greenish white).

*Calyx.*—Diameter (sepal tip to sepal tip, measured on back of flower): 36.66 mm.

*Sepal.*—Sepal shape: Elliptical. Sepal apex: Convex. Sepal margin: Smooth to serrate (mostly smooth). Color of upper side: RHS 144A (Strong yellowish green). Color of lower side: RHS 139C (Moderate yellowish green). Length (sepal tip to point of attachment to receptacle): 14.22 mm. Width: 7.03 mm. Typical and observed sepal number: 11.20.

Fruit truss:

*Length (from crown to base of terminal flower or fruit).*—21.25 cm.

*Diameter (at the base of truss).*—2.48 mm.

*Number of berries per fruiting truss (count flowers, berries, and "stumps").*—1.40.

*Color of truss.*—RHS 150C (Brilliant yellowish green).

Fruit:

*Length.*—44.03 mm.

*Width.*—40.48 mm.

*Length/width ratio.*—1.1.

*Fruit hollow length.*—9.75 mm.

*Fruit hollow width.*—4.76 mm.

*Fruit hollow length/width ratio.*—2.

*Fruit weight.*—26.9 g/fruit.

*Shape.*—Conical.

*Differences in shape between primary and secondary fruit.*—None or very slight.

*Color.*—RHS 46B (Vivid red).

*Evenness of color.*—Even or very slightly uneven.

*Glossiness.*—Strong.

*Width of the band without achenes.*—Narrow.

*Firmness.*—Firm.

*Achenes.*—Position of achenes: Level with surface. Color of achenes: RHS 34A (Vivid reddish orange). Number of achenes per fruit: 276. Achene weight: 5 mg.

*Peduncle.*—Peduncle length: 17.5 cm. Peduncle diameter: 4.6 mm.

*Position of calyx attachment.*—Level with fruit.

*Attitude of sepals.*—Outwards.

*Color of flesh (excluding core).*—RHS 33A (Vivid reddish orange).

*Color of core.*—RHS 33B (Vivid reddish orange).

*Titratable acidity (as citric acid content).*—0.94%.

*Sugar content (as soluble solids in brix).*—8.3°.

Production:

*Flowering interval.*—November to late March.

*Harvest interval.*—Late November to early April.

*Type of bearing.*—Partially remontant.

*Productivity.*—0.588 kg to 0.946 kg of fruit per plant per season from seven-month-old plants when grown in Plant City, Hillsborough County, Fla.

Resistance to diseases, pests, and abiotic stress:

*Heat.*—Moderately resistant.

*Rain damage.*—Moderately resistant.

*Two-spotted spider mite (tetranychus urticae).*—Moderately resistant.

*Botrytis fruit rot (botrytis cinerea).*—Susceptible.

*Powdery mildew (podosphaera inacularis).*—Moderately resistant.

*Anthracnose crown rot (colletoirichum aculatum).*—Highly susceptible.

*Charcoal rot (macrophomina phaseolina).*—Highly susceptible.

*Angular leaf spot (xanihomonas fragariae).*—Moderately resistant.

COMPARISON WITH PARENTAL AND COMMERCIAL VARIETIES

'DrisStrawSeventy' differs from the proprietary female parent '139T272' (unpatented) in that 'DrisStrawSeventy' is more vigorous and begins production earlier than '139T272'. In addition, fruit of 'DrisStrawSeventy' are larger, softer, lighter in color, and have a more consistent and conic shape than fruit of '139T272'.

'DrisStrawSeventy' differs from the male parent and commercial variety 'DrisStrawTwentyFour' (U.S. Plant Pat. No. 23,378) in that 'DrisStrawSeventy' has a semi-upright plant growth habit, inflorescence above foliage, achenes level with fruit surface, and calyx attachment level with fruit, whereas 'DrisStrawTwentyFour' has a spreading plant growth habit, inflorescence beneath foliage, achenes above fruit surface, and calyx attachment raise from fruit. Further, production of 'DrisStrawSeventy' begins a few days later than 'DrisStrawTwentyFour', and even though early yield of 'DrisStrawSeventy' does not typically reach the level of 'DrisStrawTwentyFour', 'DrisStrawSeventy' tends to meet or exceed 'DrisStrawTwentyFour' for late and total yield by end of March. Moreover, fruit of 'DrisStrawSeventy' are larger, and has better shelf life and flavor than fruit of 'DrisStrawTwentyFour'.

'DrisStrawSeventy' differs from the commercial variety 'DrisStrawSixtyFour' (U.S. Plant Pat. No. 30,936) in that 'DrisStrawSeventy' has a semi-upright plant growth habit, an obtuse shape of base of terminal leaflet, a straight shape in cross section of terminal leaflet, and calyx attachment level with fruit, whereas 'DrisStrawSixtyFour' has a spreading growth habit, a rounded shape of base of terminal leaflet, a concave shape in cross section of terminal leaflet, and calyx attachment inserted in fruit.

'DrisStrawSeventy' differs from the commercial variety 'DrisStrawFortyNine' (U.S. Plant Pat. No. 27,682) in that 'DrisStrawSeventy' has a semi-upright plant growth habit, an obtuse shape of base of terminal leaflet, a straight shape in cross section of terminal leaflet, and calyx attachment level with fruit, whereas 'DrisStrawFortyNine' has a semi-upright to spreading plant growth habit, a rounded shape of base of terminal leaflet, a concave to straight shape in cross section of terminal leaflet, and calyx attachment inserted in fruit.

We claim:

1. A new and distinct variety of strawberry plant named 'DrisStrawSeventy' as shown and described herein.

* * * * *